US008298664B2

(12) United States Patent
Jia (10) Patent No.: US 8,298,664 B2
(45) Date of Patent: Oct. 30, 2012

(54) FIBER-REINFORCED COMPOSITE DENTAL MATERIALS AND METHOD OF MANUFACTURE

(75) Inventor: Weitao Jia, Wallingford, CT (US)

(73) Assignee: Pentron Clinical Technologies, LLC, Wallingford, CT (US)

( * ) Notice: Subject to any disclaimer, the term of this patent is extended or adjusted under 35 U.S.C. 154(b) by 1380 days.

(21) Appl. No.: 11/734,292

(22) Filed: Apr. 12, 2007

(65) Prior Publication Data

US 2008/0250974 A1    Oct. 16, 2008

(51) Int. Cl.
  B32B 19/00   (2006.01)
  A61C 5/08    (2006.01)
  D02G 3/00    (2006.01)
(52) U.S. Cl. ........ 428/357; 433/220; 433/224; 428/377; 428/378
(58) Field of Classification Search .................. 523/116, 523/117; 433/220, 224, 180, 215, 221, 225, 433/226; 428/375–396; 57/211–242
See application file for complete search history.

(56) References Cited

U.S. PATENT DOCUMENTS

| | | | |
|---|---|---|---|
| 3,066,112 A | 11/1962 | Bowen | |
| 3,179,623 A | 4/1965 | Bowen | |
| 3,194,784 A | 7/1965 | Bowen | |
| 3,715,331 A | 2/1973 | Molnar et al. | |
| 3,751,399 A | 8/1973 | Lee, Jr. et al. | |
| 3,926,906 A | 12/1975 | Lee, II et al. | |
| 4,544,359 A | 10/1985 | Waknine | |
| 4,547,531 A | 10/1985 | Waknine | |
| 4,622,012 A * | 11/1986 | Smoler | 433/221 |
| 4,717,341 A | 1/1988 | Goldberg et al. | |
| 4,894,012 A | 1/1990 | Goldberg | |
| 5,088,927 A | 2/1992 | Lee | |
| 5,275,562 A | 1/1994 | McSpadden | |
| 5,276,068 A | 1/1994 | Waknine | |
| 5,415,546 A | 5/1995 | Cox, Sr. | |
| 5,444,104 A | 8/1995 | Waknine | |
| 5,564,929 A | 10/1996 | Alpert | |
| 5,684,103 A | 11/1997 | Jia et al. | |
| 5,741,139 A | 4/1998 | Sicurelli, Jr. et al. | |
| 5,797,748 A * | 8/1998 | Reynaud et al. | 433/224 |
| 5,816,816 A | 10/1998 | Scharf | |
| 5,873,725 A * | 2/1999 | Perler et al. | 433/221 |
| 6,013,694 A | 1/2000 | Jia et al. | |
| 6,186,791 B1 | 2/2001 | Karmaker | |
| 6,267,597 B1 * | 7/2001 | Kim | 433/224 |
| 6,270,562 B1 | 8/2001 | Jia | |
| 6,287,122 B1 | 9/2001 | Seeram et al. | |
| 6,417,246 B1 | 7/2002 | Jia et al. | |
| 6,428,319 B1 | 8/2002 | Lopez et al. | |
| 6,439,890 B1 | 8/2002 | Karmaker et al. | |
| 6,443,730 B2 | 9/2002 | Davidson | |
| 6,447,297 B1 | 9/2002 | Lopez et al. | |

(Continued)

Primary Examiner — Jennifer Chriss
Assistant Examiner — Ricardo E Lopez
(74) Attorney, Agent, or Firm — Wood, Herron & Evans, LLP (57) ABSTRACT

A dental material comprising a symmetrically rod-shaped fiber-reinforced composite comprising at least two layers of preimpregnated fibers, wherein the preimpregnated fibers comprise fibers coated with a resin, wherein the layers are unbraided, and wherein each layer is unidirectionally disposed on the preceding layer in a direction that is different from the direction of the preceding layer. The rod-shaped composite may be hollow and contain a channel throughout the axial length of the rod or may contain a shaft or other material that is inserted into the channel.

32 Claims, 4 Drawing Sheets

U.S. PATENT DOCUMENTS

| | | |
|---|---|---|
| 6,827,576 B2 | 12/2004 | Karmaker et al. |
| 7,086,864 B2 | 8/2006 | Lopez et al. |
| 7,163,401 B2 | 1/2007 | Karmaker et al. |
| 7,168,952 B2 | 1/2007 | Karmaker et al. |
| 7,186,760 B2 | 3/2007 | Rudo |
| 7,204,874 B2 | 4/2007 | Jia et al. |
| 7,204,875 B2 | 4/2007 | Jia et al. |
| 2003/0027102 A1* | 2/2003 | Karmaker et al. ............ 433/220 |
| 2003/0113691 A1 | 6/2003 | Ben-Yaakov et al. |
| 2004/0086446 A1 | 5/2004 | Jia et al. |
| 2004/0241609 A1 | 12/2004 | Jia et al. |
| 2006/0208393 A1 | 9/2006 | Karmaker |
| 2006/0241205 A1 | 10/2006 | Jia |

\* cited by examiner

FIBER-REINFORCED COMPOSITE DENTAL MATERIALS AND METHOD OF MANUFACTURE

TECHNICAL FIELD

This invention relates to a process for forming dental composite structures comprising fiber reinforcement for use as dental restorative materials, implants, orthodontic and endodontic appliances. More specifically, the fiber-reinforced composite structure is a pre-fabricated cylindrically symmetrical medical/dental device to be used for dental materials to restore, at least in part, the function of a tooth to be repaired, or an implant for bone or tooth, or a fixture in dental orthodontic applications and whereby the composite structure is machinable.

BRIEF DESCRIPTION OF THE RELATED ART

Dental resins are polymeric materials that are used to construct dental structures such as restorations, prostheses and appliances. They exhibit relatively poor stress-bearing properties. In order to enhance the stress-bearing properties of dental resins and to minimize crack propagation, fiber reinforcements have been incorporated within dental resins. Fiber-reinforced dental resins are anisotropic materials that derive their strength and stiffness from reinforcing fibers embedded within the resin. The orientation of the reinforcing fibers provides directionality to the properties and performance attributes of the resin. The properties and performance attributes of fiber-reinforced dental resins include, for example, the ability of the resin to resist an externally applied shearing force perpendicular to the long axis of the fiber-reinforced device. It is common that the fibers loosen from the matrix when it is cut or drilled. Moreover, glass fiber reinforced dental composite posts are low in radiopacity, and it is often more expensive to custom produce radiopaque glass fibers for dental use.

Resins that include reinforcing fibers that are all oriented in one direction are restricted in some way in their performance in the direction of the reinforcing fibers. Thus, for example, the ability of a resin that includes reinforcing fibers that are all oriented in one direction to resist a shearing force applied in a direction parallel to the axis of the reinforcing fibers approaches that of the unreinforced resin. Additionally, prior to curing, the resin structure is unstable since it can easily shear, which makes the fiber arrangement/structure out of order, causing fiber spreading, for example, and therefore forming a weak structure.

Numerous attempts to improve the structures of unidirectional fiber oriented composites have been reported utilizing twisted fiber orientation, biaxial weaves, and even triaxial weaves of the fiber orientations. U.S. Pat. No. 5,816,816 to Scharf, hereby incorporated by reference, teaches a method of making a dental post using a woven fabric tube to fill the canal with a dental composite. While it appears to be easy to make a post in such a way, the limitations are obvious, as a dental post created in size and shape is bound by the woven tube. U.S. Pat. No. 5,741,139 to Sicurelli, Jr. et al., hereby incorporated by reference, teach using twisted fibers and/or randomly distributed fibers as the reinforcement elements in a dental post, yet, the process of making such is not disclosed. U.S. Pat. No. 7,673,550 to Karmaker et al., hereby incorporated by reference, teaches a structure of a unidirectional fiber rod wrapped with a layer of woven fabric. A sleeve made of such woven fabric is suggested to wrap on the fiber rod. U.S. Pat. No. 7,186,760 to Rudo, hereby incorporated by reference, teaches using triaxial braided fabric for reinforcing dental resins. The fabric is cut and wetted with dental resin and used as a patch or patches layered between the dental resin to repair/restore a tooth. U.S. Pat. No. 6,287,122 to Seeram et al., hereby incorporated by reference, teach a fiber-reinforced composite post product with graded stiffness. Although the '122 patent uses a conventional filament winding method for winding filament at various orientations onto a mandrel to form a post, it does not disclose or imply that there are at least two layers of the fibers overlaying each other. It teaches intentionally layering in such a way as to provide graded stiffness along the length of the post. U.S. Pat. No. 6,443,730 to Davidson, hereby incorporated by reference, teaches a break-resistant composite structure for a dental endodontic instrument using partially twisted and off-axis oriented fibers as the instrument core and a polymer composition containing abrasive particles molded onto the core.

Accordingly, there is a need for a better method of constructing, reinforcing or modifying dental structures so that they are mechanically stable and can resist external forces applied from various directions. There accordingly remains a need in the art for producing fiber-reinforced dental structures that are mechanically durable and high in shear strength.

SUMMARY OF THE INVENTION

These and other objects and advantages are accomplished by a dental material having a symmetrically rod-shaped fiber-reinforced composite structure including at least two layers of preimpregnated fibers, wherein the preimpregnated fibers are fibers preimpregnated or coated with a resin, wherein the layers are unbraided, and wherein each layer is unidirectionally disposed on the preceding layer in a direction that is different from the direction of the preceding layer. The rod-shaped composite may be hollow and contain a channel throughout the axial length of the rod or may contain a shaft or other material that is inserted into the channel.

In a preferred embodiment of the invention, one fiber layer is applied onto a shaft in a direction angled from right to left and a second fiber layer is applied onto the shaft and first layer in a direction angled from left to right, wherein the application of fiber layers continues until the desired thickness is achieved.

In a preferred embodiment of the method of the invention, a material for medical or dental use is fabricated wherein a shaft is provided, a first fiber is wound onto the shaft, wherein the fiber is pre-impregnated with a curable resin matrix material to form a first layer, a second fiber is wound onto the shaft, wherein the second fiber is pre-impregnated with a curable resin matrix material to form a second layer, wherein the direction/orientation of the first fiber is different than the direction of the second fiber, wherein the fibers are pulled and maintained under tension or pressure, and wherein the resin matrix material is cured while the fibers are maintained in tension and/or pressure.

In an embodiment of the method of using the invention, a hollow post is provided having a channel therein. The post is fabricated by providing a shaft and winding a first fiber onto the shaft in a first direction to form a first layer, wherein the fiber is pre-impregnated with a curable resin matrix material. A second fiber is wound onto the shaft in a second direction to form a second layer, wherein the second fiber is pre-impregnated with a curable resin matrix material, wherein the first direction is different from the second direction. The fibers are pulled and maintained under tension or pressure and the resin matrix material is cured while the fibers are maintained in tension or pressure. Thereafter, the shaft is removed to provide a channel in the post, wherein holes are drilled into the post at various locations. For insertion into the patient's mouth, a bonding agent and/or cement is applied to the walls of a patient's root canal. The post is inserted into the patient's root canal. Optionally, prior to insertion into the root canal, the channel of the post may be filled with a cement, bonding agent, filling material, therapeutic material or other resinous material useful in dental and endodontic treatment, or alternatively, the hollow post may be inserted into the canal and when in the canal, it may be filled with a cement, bonding agent, filling material, therapeutic material or other resinous material useful in dental and endodontic treatment. Some of the material filled into the channel is expelled through the holes in the post and is bonded to the bonding agent/cement in the patient's root canal.

BRIEF DESCRIPTION OF THE DRAWINGS

Features of the present invention are disclosed in the accompanying drawings, wherein similar reference characters denote similar elements throughout the several views and wherein.

DETAILED DESCRIPTION OF THE PREFERRED EMBODIMENTS

The principles and operation of the dental/medical materials of the present invention may be better understood with reference to the drawings and the accompanying description.

Figure 1:
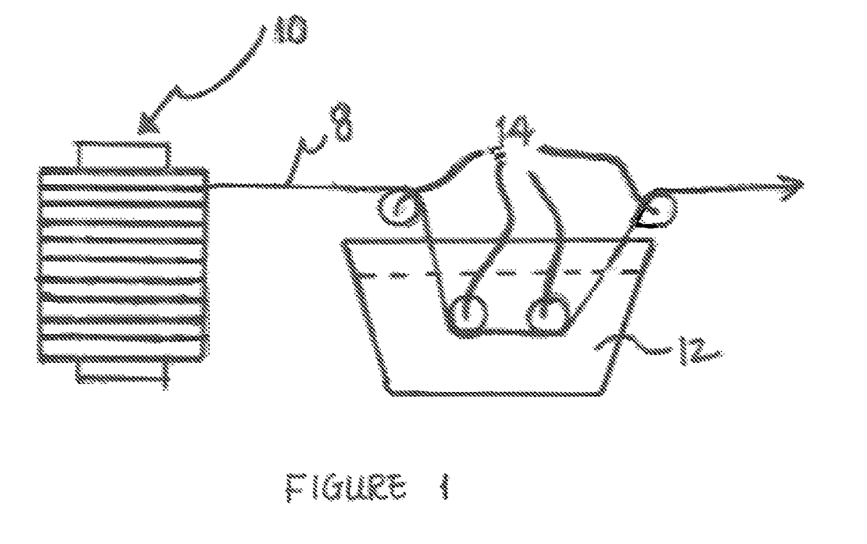
FIG. 1 is a schematic view of a fiber coating process.

FIG. 1 shows a method of impregnating resin onto a fiber wherein a fiber strand 8 from a spool of fiber 10 is guided into a resin bath 12. The fiber may be of any known fiber material in the art including, but not limited to, polymeric, glass, ceramic or metal. Examples of polymeric fibers include, but are not limited to, cellulose, silk, polyethylene, polyamide, aramid, polyester, polyaramid, acrylic, vinyl and modacrylic, polyolefin, polytetrafluorethylene, or mixtures thereof. Examples of glass and ceramic fibers include quartz glass, borosilicate glass, lithium aluminum silicate, barium aluminum silicate, strontium, zinc glass, boron, silicon carbide, colloidal silica, zirconia, carbon and graphite. The fiber may be in the form of a single fiber, a bundle of fibers, tape or fabric.

The resin bath may contain any thermoset or thermoplastic resin selected from those known in the art of dental materials. Examples of thermoplastic resins include, but are not limited to, polyethylene, polypropylene, polysulfone, polycarbonate, polyimide, epoxy-based materials, polyester, polyolefin, acrylic, methacrylic monomer, polyolefin, polyurethane, styrene and mixtures thereof, styrene acrylonitriles, polyamides, polyesters, polyolefins, polyimides, polyacrylates, polyurethanes, vinyl esters, epoxy-based materials, ABS polymers, polysulfones, polyacetals, polycarbonates, polyphenylene sulfides, synthetic or natural rubber, and the like. It is preferable that the fibers to be resin pre-impregnated are different in nature or composition from the resin coating thereon. When using a thermoplastic resin, curing of the composite structure is performed after fiber winding. If curing by heat, it is sufficiently heated to a point to melt the polymer matrix and then allow the temperature to cool down to harden the polymer and form the fiber reinforced composite structure.

Examples of thermosetting resins include all those known in the art and which are suitable for uses in dentistry and medicine. Preferred examples include those based on acrylic and methacrylic monomers, for example those disclosed in U.S. Pat. Nos. 3,066,112, 3,179,623, and 3,194,784 to Bowen; U.S. Pat. Nos. 3,751,399 and 3,926,906 to Lee et al.; commonly assigned U.S. Pat. Nos. 5,276,068 and 5,444,104 to Waknine; and commonly assigned U.S. Pat. No. 5,684,103 to Jia et al., the pertinent portions of all which are herein incorporated by reference. An especially preferred methacrylate monomer is the condensation product of bisphenol A and glycidyl methacrylate, 2,2'-bis[4-(3-methacryloxy-2-hydroxy propoxy)-phenyl]-propane (hereinafter abbreviated "BIS-GMA"). Polyurethane dimethacrylates (hereinafter abbreviated "PUDMA"), triethylene glycol dimethacrylate (hereinafter abbreviated "TEGDMA"), polyethylene glycol dimethacrylate (hereinafter abbreviated "PEGDMA"), urethane dimethacrylate (hereinafter abbreviated "UDMA"), hexane diol dimethacrylate (hereinafter abbreviated "1,6 HDDMA") and polycarbonate dimethacrylate (hereinafter abbreviated "PCDMA") are also commonly-used principal polymers suitable for use in the present invention. Epoxy based resins, vinyl silicones, and other polymerizable unsaturated resins are also options.

The polymeric matrix typically includes polymerization initiators, polymerization accelerators, ultraviolet light absorbers, anti-oxidants, and other additives well known in the art. The polymeric matrices may be visible light curable, self-curing, dual curing, and vacuum, heat, and pressure curable compositions as well as any combination thereof. The visible light curable compositions include the usual polymerization initiators, polymerization accelerators, ultraviolet absorbers, fluorescent whitening agents, and the like. Preferred light curing initiators include camphorquinone (CQ) and trimethyl benzoyl phosphine oxide (TPO). The heat curable compositions, which are generally filled compositions, include, in addition to the monomeric components, a heat cure initiator such as benzoyl peroxide, 1,1'-azobis (cyclohexanecarbonitrile), or other free radical initiators. The preferred polymeric matrix can be a curable matrix, wherein light cure effects partial cure of the matrix, and final curing is by heat under controlled atmosphere. It is possible to cure the polymeric matrix by heating followed by light curing as taught in U.S. Patent Application Publication No. 20040241609 to Jia et al., which is hereby incorporated by reference. Radiopaque agents and/or fillers may be included in the matrix, as commonly known for dentistry and medicine.

The amount of a filler is usually determined by the specific use of the fiber-reinforced composite. Generally, the filler is added in an amount sufficiently to enhance the radiopacity or property of the final fiber reinforced composite structure and is up to about seventy percent by weight of the composite and preferably in an amount of up to about thirty percent by weight of the composite. Suitable fillers are those capable of being covalently bonded to the polymeric matrix itself or to a coupling agent that is covalently bonded to both. Examples of suitable filling materials include but are not limited to those known in the art such as silica, silicate glass, quartz, barium based fillers such as barium silicate, barium sulfate, barium molybdate, barium methacrylate, barium yttrium alkoxy ($Ba_2Y(OR)_x$), barium borosilicate, bismuth based fillers, strontium based fillers such as strontium silicate, strontium borosilicate, ytterbium based fillers, borosilicate, lithium silicate, amorphous silica, ammoniated or deammoniated calcium phosphate and alumina, zirconia, tin oxide, tantalum oxide, niobium oxide, and titanic. Particularly suitable fillers for dental filling-type materials prepared in accordance with this invention are those having a particle size ranging from about 0.1-5.0 microns with a silicate colloid of 0.001 to about 0.07 microns and prepared by a series of milling steps comprising wet milling in an aqueous medium, surface etch milling and silanizing milling in a silane solution. Some of the aforementioned inorganic filling materials are disclosed in commonly-assigned U.S. Pat. Nos. 4,544,359 and 4,547,531 to Waknine, U.S. Pat. Nos. 6,013,694 and 6,417,246 to Jia et al., U.S. Pat. No. 6,270,562 to Jia, Patent Application Publication No. 20040086446 to Jia et al., and Patent Application Publication No. 20060241205 to Jia, the pertinent portions of which are incorporated herein by reference. Suitable organic filler materials are known in the art, including for example the poly(methacrylate) fillers described in U.S. Pat. No. 3,715,331 to Molnar. A mixture of organic and inorganic filler materials may also be used.

With respect to the fiber, it is preferable that the fiber be a single fiber or bundle of fibers or fabric in the form of a thin strand so that it can be easily wound onto a shaft. The fiber 10 is pulled through the resin bath 12 to coat the resin onto the fiber. A series of bobbins or reels 14 may be used to guide fiber 10 into resin bath 12. After the fiber is coated with resin it is wound or wrapped onto a shaft, rod, bar, wire, tube or similar component having an axis. It may have a smooth, roughened, serrated, threaded or irregular surface. Furthermore, it may be in any known shape such as cylindrical, triangular, rectangular, square, oval or the like.

Alternatively, in a process of making a fiber reinforced composite material, a polymerizable resin compound is applied to the shaft, and thereafter, a fiber layer is subsequently formed by winding uncoated fiber onto the resin coated shaft. Before winding another layer of the fiber onto the previous fiber layer, another coat of the resin is applied onto the fiber layer to cover the uncoated fiber surfaces and further binding to the first resin layer applied to the shaft. Additional resin layers and fiber layers are applied as desired to attain the necessary thickness. Each fiber layer can be cured individually or cured together upon completion of application of the fiber layers. Alternatively, instead of using uncoated fibers, resin-coated or impregnated fibers may be used herein.

The shaft or bar may be solid or hollow and may be fabricated of any material known in the art including, but not limited to, metal, ceramic, glass, or polymeric or resinous material, or their combinations. The bar may be chemically or mechanically abraded prior to use so as to provide good adhesion between the bar and the layers of fibers applied thereto, which is preferable if the bar is being used in the final structure. Furthermore, it is preferable that the fiber be wound onto the bar in tension so that the fiber is wound tightly around the bar and onto any preceding layers.

A first layer of fiber is applied onto the bar in a continuous direction. A second layer is applied onto the first layer of fiber in a direction different than the first layer of fiber. Additional layers of fiber may be applied until the final thickness and strength is achieved, alternating direction so that no two successive or consecutive layers are wound onto the shaft in the same direction. This layering of fibers provides a finished product that can better resist shear forces applied from any angle.

Figure 2:
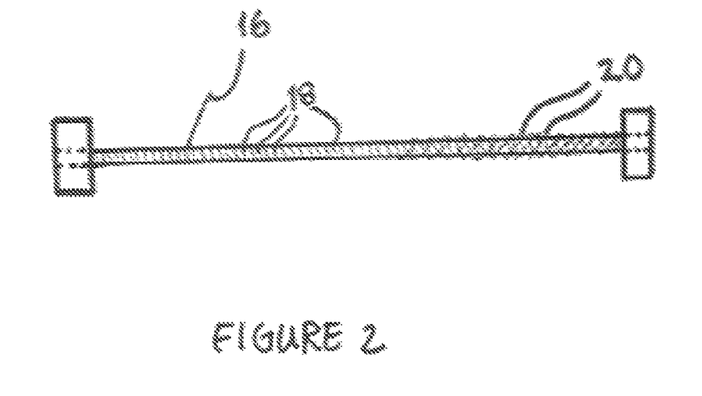
FIG. 2 is a schematic view of a fiber winding process.
Figure 3:
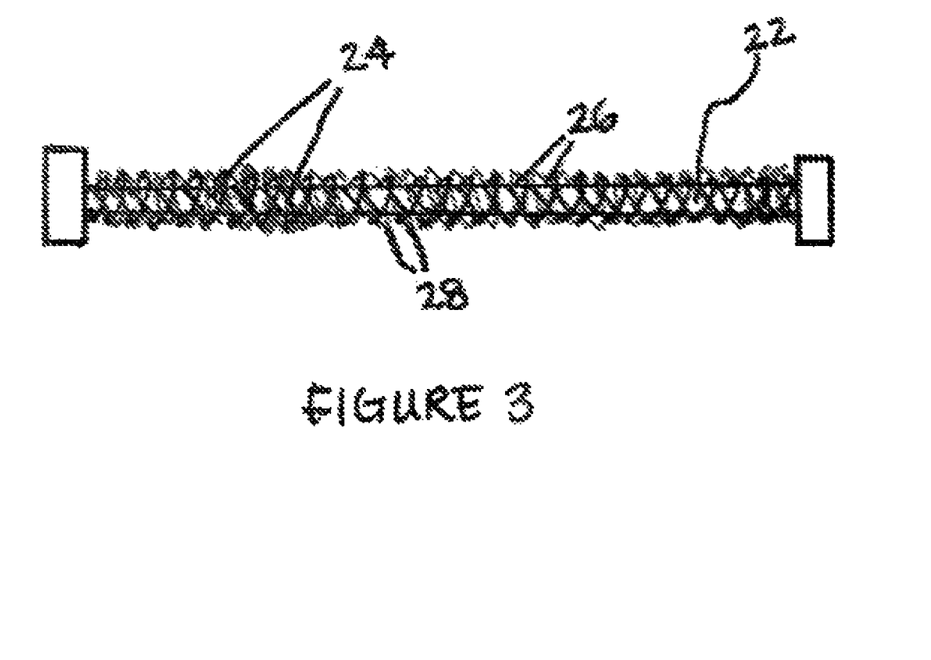
FIG. 3 is an elevational view of a bar having three layers of fiber thereon.
Figure 4:
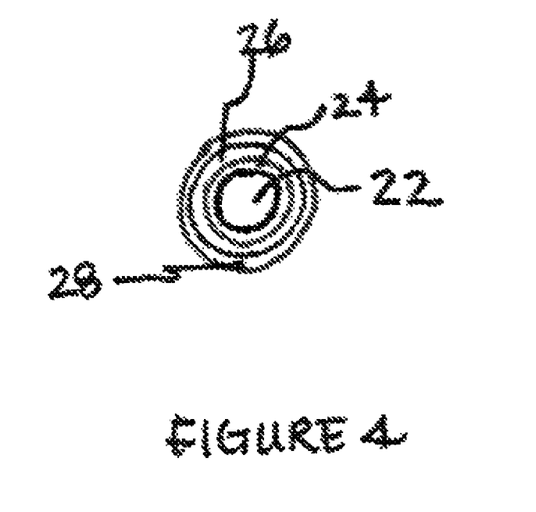
FIG. 4 is a top plan view of the bar in FIG. 3.

FIG. 2 shows a shaft 16 upon which a resin-coated fiber 18 is wound in an angled direction from left to right. A second resin-coated fiber 20 is wrapped onto shaft 16 and fiber 18 in an angled direction (from right to left) that is different from the winding direction of fiber 18. FIG. 3 shows shaft 22 having three layers of fibers 24, 26, and 28, wrapped thereon. Layer 24 is wound in a direction angled from upper left to lower right; layer 26 is wound in a direction angled from upper right to lower left; and layer 28 is wound in a direction angled from upper left to lower right. The change in direction of each fiber layer distributes the strength evenly across the entire surface of the product providing strength and integrity to the final product. As many layers of fiber as desired may be wound onto a shaft to achieve the desired strength and thickness of the product. FIG. 4 is a top plan view of shaft 22 shown in FIG. 3, with layers 24, 26 and 28 thereon.

Figure 5:
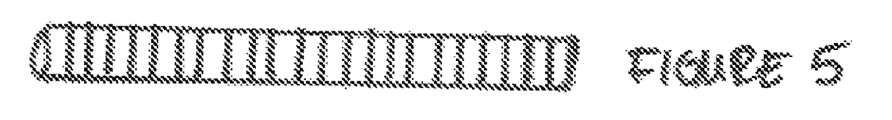
FIG. 5 is an elevational view of a bar having a fiber layer applied thereto in a direction perpendicular to the axial direction of the bar.
Figure 6:
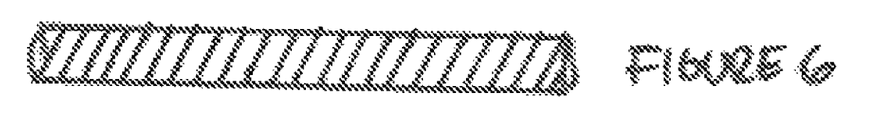
FIG. 6 is an elevational view of a bar having a fiber layer applied thereto in an angled direction, from right to left.
Figure 7:
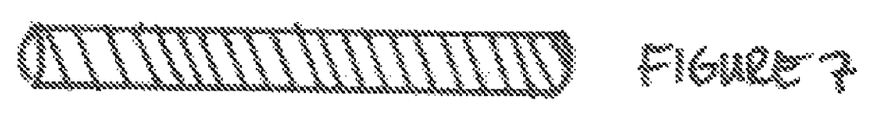
FIG. 7 is an elevational view of a bar having a fiber layer applied thereto in an angled direction, from left to right.
Figure 8:
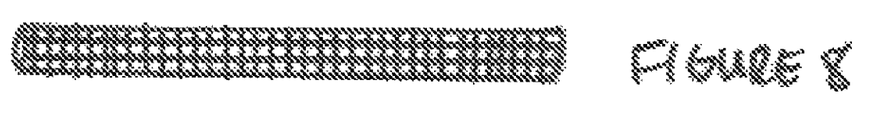
FIG. 8 is an elevational view of a bar having a fiber layer applied thereto in the form of a fabric having a grid pattern.

FIGS. 5 through 8 show examples of variations of directions in which the fibers can be wound onto a shaft. Each layer of fiber applied onto a shaft is varied in direction from layer to layer in order to provide even and consistent strength along the length and perimeter of the shaft. For example, a first fiber layer is applied in a direction that is perpendicular to the axial direction of the shaft, as shown in FIG. 5; a second fiber layer is applied in an angled direction (from upper right to lower left) as shown in FIG. 6; a third fiber layer is applied in an angled direction (from upper left to lower right) as shown in FIG. 7; a fourth fiber layer in the form of a fabric grid pattern is applied as shown in FIG. 8. The layers may be repeated in the same sequence or in different sequences or in directions additional to those shown, as long as no two consecutive layers are applied in the same direction.

Figure 9:
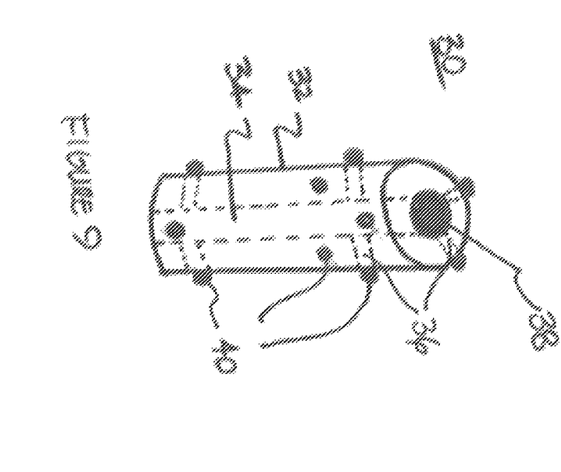
FIG. 9 is an elevational view of a bar having a filled channel and filled openings.

FIGS. 9 through 12 show variations of the shafts and fibers herein. FIG. 9 shows a component 30 having a layered fiber-reinforced composite cylinder 32 formed from the application of fibers applied onto a shaft that has been removed to provide an opening or channel 34 therethrough. The layers of fiber-reinforced composite have been cured to complete hardness and the shaft has been removed. Holes 36 have been drilled into layered-fiber-reinforced composite cylinder 32 to provide openings for resin or composite 38 to flow through, which resin 38 is inserted into opening 34. Resin 38 is filled into the entire channel 34 and further flows through holes 36 to form resin tags 40. Resin 38 and resin tags 40 are cured by light and/or by self curing initiators present in the resin or other methods known in the art. Resin tags 40 provide attachment for dental cements, sealants, adhesives, or resins that are used therewith when inserting the component into a patient's mouth or fabricating a dental restorative with the component.

In one method of using component 30 in FIG. 9 as an obturator or post, the patient is prepared for insertion of the post into the root canal. A bonding agent and/or cement is applied to the walls of a patient's root canal. Thereafter, the post is inserted into the patient's root canal. Optionally, prior to insertion into the root canal the channel of the post may be filled with a cement, bonding agent, endodontic filling material, therapeutic material or other resinous material useful in dental and endodontic treatment. Examples of filling materials include those in U.S. Pat. Nos. 7,204,874 and 7,204,875 to Jia et al., which are hereby incorporated by reference. Alternatively, the hollow post may be inserted into the canal and when in the canal, it may be filled with a cement, bonding agent, endodontic filling material, therapeutic material or other resinous material useful in dental and endodontic treatment. Some of the material filled into the channel will exit through the holes in the post and bond to the bonding agent/cement in the patient's root canal.

Figure 10:
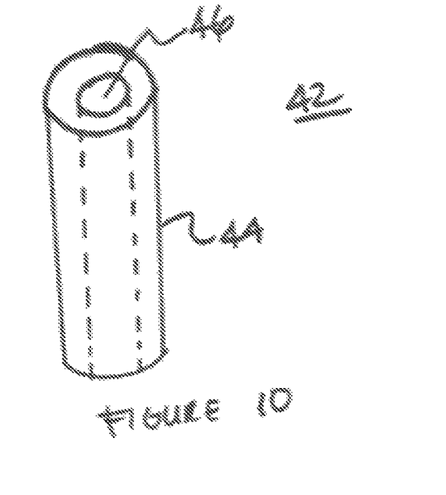
FIG. 10 is an elevational view of a bar having a channel therein.

FIG. 10 shows a component 42, such as for use as a dental post, having a layered-fiber-reinforced composite cylinder 44 formed of layers of fibers impregnated with resin or polymer and applied in alternating directions onto a shaft. The resin coated fibers may be cured after application of each layer, or may be cured after all layers have been applied. The shaft is then removed to provide a channel or opening 46 therein. The cylinder may be used as is or may be filled in with composite or resin material, or alternatively, may have a solid rod inserted therein to provide support and strength thereto.

Figure 11:
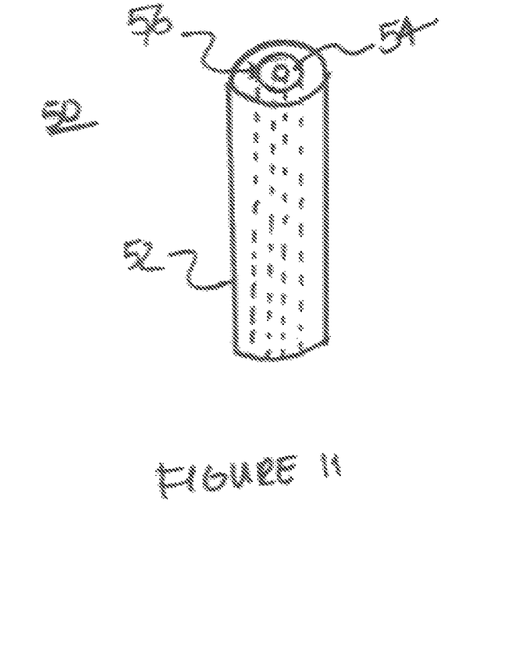
FIG. 11 is an elevational view of a bar having a hollow metal rod therein.

FIG. 11 shows a component 50 having a layered-fiber-reinforced composite cylinder 52 formed from layers of fibers as described for the component formed in FIG. 10. A hollow metal rod 54 is positioned in the central opening 56. Rod 54 is either initially used as the shaft onto which the fibers are wound, or is inserted after the layered-fiber reinforced composite cylinder is cured to hardened form and the initial shaft used for winding of fibers thereon has been removed after curing is complete. Alternatively, metal rod 54 may be solid or fabricated of a material other than metal such as, but not limited to, ceramic, polymeric, resin or glass material.

Figure 12:
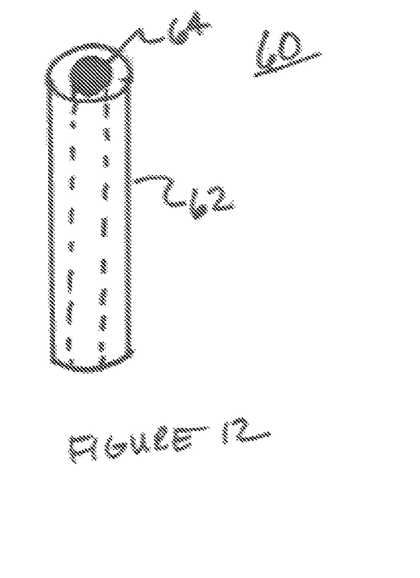
FIG. 12 is an elevational view of a bar having a shaft therein.

FIG. 12 shows yet another alternative to the embodiments herein wherein a component 60 has a layered-fiber-reinforced composite cylinder 62 with a shaft or rod 64 therein. Shaft 64 may be mechanically or chemically abraded to assist in adherence of the fiber layers onto shaft 64. Shaft 64 may be fabricated of ceramic, glass, polymeric or metal material.

The fiber reinforced composite material is preferably formed into a dental post, but it may be used for a variety of dental and medical devices including, but not limited to, orthodontic retainers, bridges, space maintainers, tooth replacement appliances, splints, crowns, partial crowns, dentures, teeth, jackets, inlays, onlays, facings, veneers, facets, implants, abutments, cylinders, and connectors.

When used as a post, the length may vary between about 6 mm and 25 mm and the diameter may vary from about 0.5 mm to about 3 mm. Depending upon the use of the material produced, the shaft or the opening left from the shaft after it is removed is in the range of about 0.1 mm to about 30 mm in diameter. Moreover, the fiber reinforcement in the composite structures herein are uniform and evenly spread and bonded. Common rotary machining methods to surface finish the rods can be performed to create any surface features, such as serrated form, screw shaped, tapered, dumbbell-shaped, or other symmetrical forms. The rods formed may be cleaned afterwards and surface treated further.

The following non-limiting example illustrates the invention.

EXAMPLE 1

Fabrication of a Dental Post Precursor

In this case, a manual operation of winding fibers onto a shaft is illustrated. A 5-inch-long stainless steel tube with an external diameter of about 0.6 mm (a 23 gauge hypodermic tube according to ISO 9626 specification) is chosen to use as the center shaft/core and intended to be part of the post composite structure. Since a dental post suitable for inserting into a tooth root canal is usually of smaller diameters of about 0.8-2.0 mm, the 23 gauge tube with the fiber reinforced structure thereon will provide the desired size for root canal treatment.

The procedure involves coating the entire steel tube surface with a thin layer of polymerizable Opaque White resin (Lute-It® Stains Kit, Pentron Clinical Technologies, LLC) with a brush to mask the metal color and light curing the surface for 1 minute in the Sculpture ('?) light curing box (Pentron Clinical Technologies, LLC) to polymerize the resin opaque layer. This opaque resin layer blocks the underneath metal color and is not movable when the fiber layers are wound and cured to form the post structure. Following application of the opaque layer, one end of the tube is clamped with a dental hand piece (Model XL-030, OSADA Electric Co., Ltd, Tokyo, Japan) and the other end of the tube is unclamped and free and accessible to a rotation action, by hand spinning, for example. The dental hand-piece clamping device also serves as a bearing in this case.

A fiber strip is prepared using a continuous fiber strand of S glass (a glass fiber bundle made of about 2000 S glass fiber filaments, Product Code: 463 AA 1250, Owens Corning, Pa.) and is treated/impregnated with a polymerizable resin (as illustrated in FIG. 1 using a resin compound described in U.S. Pat. Nos. 4,717,341 and 4,894,012 to Goldberg and hereby incorporated by reference), to form a fiber strip (tape) of about 2 mm width. The fiber strand is first fixed or bonded to one end of the coated metal tube with a drop of dental Flow-It® composite (available from Pentron Clinical Technologies, LLC). The composite is light cured for about 2 seconds with a portable LED light (Avante™ LED, Pentron Clinical Technologies, LLC) to prevent the fiber strand from loosening during winding and to maintain it under tension.

While holding the fiber with one hand, the tube is rotated or spun to provide winding of the fiber upon the tube. The fiber strand is wound onto the shaft from the left end of the tube toward the right side in an angled orientation, and in such a way that the fiber loops are parallel to each other and aligned side by side intimately, forming a first layer of fiber on the tube. When the fiber strand reaches the opposite end of the tube that is clamped, the fiber is bonded to the tube using the dental Flow-It® composite to maintain the tension and prevent fiber loosening.

A second layer is applied onto the tube in the same way as the first layer, but in a direction different than the orientation of the first fiber layer. This winding process continues for application of four layers of fiber onto the tube. Upon completion of the fourth layer, a thin layer of Flow-It® flowable composite is coated onto the wound fiber surface to give a complete surface seal with a dental brush. The clamping device is removed and the fiber layers are light cured in a Sculpture™ light curing box for 2 minutes. The final diameter of the cured rod is about 2.2 mm. The composite rod structure is then cut and machined to form any dimension or size as desired from about 0.8-2 mm diameters with lengths of about 6-25 mm to be suitable for a dental post. The dental posts obtained are now ready to be used in root canal treatment or to restore a broken tooth. The post surfaces can be further chemically treated or resin coated to enhance the bonding between a cementing media and the post in the restoration procedure.

While the invention has been described with reference to exemplary embodiments, it will be understood by those skilled in the art that various changes may be made and equivalents may be substituted for elements thereof without departing from the scope of the invention. In addition, many modifications may be made to adapt a particular situation or material to the teachings of the invention without departing from the essential scope thereof. Therefore, it is intended that the invention not be limited to the particular embodiment disclosed as the best mode contemplated for carrying out this invention, but that the invention will include all embodiments falling within the scope of the appended embodiments.

What is claimed is:

1. A material for dental or medical use comprising: a symmetrically rod-shaped fiber-reinforced composite comprising a metal shaft and at least two layers of impregnated fibers wound directly on the metal shaft to be in direct adhering contact with the metal surface of the metal shaft, wherein the impregnated fibers comprise fibers coated with a resin; wherein the layers are unbraided; and wherein each layer is unidirectionally disposed on the preceding layer in a direction that is different from the direction of the preceding layer.

2. The material of claim 1 wherein the fibers comprise glass, ceramic, polymer or mixtures thereof.

3. The material of claim 1 wherein the metal shaft is a solid rod.

4. The material of claim 2 wherein the polymeric fibers comprise cellulose, silk, polyethylene, polyamide, aramid, polyester, polyaramid, acrylic, vinyl and modacrylic, polyolefin, polytetrafluorethylene, or mixtures thereof.

5. The material of claim 2 wherein the glass fibers comprise quartz, borosilicate, lithium aluminum silicate, barium aluminum silicate, zinc, boron glass or mixtures thereof.

6. The material of claim 2 wherein the ceramic fibers comprise strontium, silicon carbide, colloidal silica, zirconia or mixtures thereof.

7. The material of claim 1 wherein the fibers are impregnated with a thermoplastic or thermoset resin.

8. The material of claim 1 wherein the fibers each comprise a single fiber, a bundle of fibers, fiber tape or fiber fabric.

9. The material of claim 1 wherein the fibers are impregnated with a resin comprising polyethylene, polypropylene, polysulfone, polycarbonate, polyimide, epoxy-based materials, polyester, acrylic, methacrylic, polyolefin, polyurethane, styrene, styrene acrylonitriles, polyamides, polyacrylates, vinyl esters, ABS polymers, polyacetals, polyphenylene sulfides, synthetic rubber, natural rubber, vinyl silicones and mixtures thereof.

10. The material of claim 9 wherein the methacrylic material comprises a condensation product of bisphenol A and glycidyl methacrylate, 2,2'-bis[4-(3-methacryloxy-2hydroxy propoxy)-phenyl]-propane (BIS-GMA), polyurethane dimethacrylates (PUDMA), triethylene glycol dimethacrylate (TEGDMA), polyethylene glycol dimethacrylate (PEGDMA), urethane dimethacrylate (UDMA), hexane diol dimethacrylate (1,6 HDDMA) and polycarbonate dimethacrylate (PCDMA), or a mixture thereof.

11. The material of claim 1 wherein the resin comprises a filler material.

12. The material of claim 11 wherein the filler material comprises silica, silicate glass, quartz, barium based fillers such as barium silicate, barium sulfate, barium molybdate, barium methacrylate, barium yttrium alkoxy ($Ba_2Y(OR)_x$), barium borosilicate, bismuth based filters, strontium based fillers such as strontium silicate, strontium borosilicate, ytterbium-based fillers, borosilicate, lithium silicate, amorphous silica, ammoniated or deammoniated calcium phosphate and alumina, zirconia, tin oxide, tantalum oxide, niobium oxide, titania or mixtures thereof.

13. The material of claim 1 wherein the metal shaft is a hollow tube.

14. The material of claim 13 wherein an exterior surface of the hollow tube is abraded to increase adhesion to the layers.

15. The material of claim 1 wherein the metal shaft is cylindrical, triangular, rectangular, square or oval in cross-sectional shape.

16. A method of fabricating the material of claim 1, comprising:
providing the metal shaft;
disposing the at least two layers of impregnated fibers around the metal shaft by:
winding a first fiber onto the metal shaft in a first direction to form a first layer,
winding a second fiber onto the metal shaft in a second direction different from the first direction to form a second layer, and
optionally winding additional fibers onto the metal shaft to form additional layers wherein each succeeding additional layer is wound in a direction that is different from the preceding layer,
wherein the first, second and additional layers each comprise the respective first, second and additional fiber impregnated with a curable resin matrix material;
placing the first, second and additional fibers in tension or under pressure; and
curing the resin matrix material while the fibers are maintained in tension or under pressure to form the at least two layers of impregnated fibers.

17. The method of claim 16 wherein the first, second and additional fibers are pre-impregnated with the curable resin matrix material prior to winding onto the metal shaft.

18. The method of claim 16 wherein the metal shaft is hollow thereby having an empty space therein, and wherein the method further comprises, after the windings, filling the empty space with a polymeric, glass, resin, ceramic or metal material.

19. A material for dental or medical use comprising:
a symmetrically rod-shaped fiber-reinforced composite comprising a hollow metal shaft and a plurality of layers of resin-coated glass fibers wound directly on the hollow metal shaft to be in direct adhering contact with the metal surface of the metal shaft, and an exterior surface of the hollow metal shaft is abraded to increase adhesion to the plurality of layers, wherein the plurality of layers are unbraided; and wherein each of the plurality of layers is unidirectionally disposed on the preceding layer in a direction that is different from the direction of the preceding layer.

20. The material of claim 19, wherein the resin-coated glass fibers each comprise a single fiber, a bundle of fibers, a fiber tape or a fiber fabric pre-impregnated with the resin before being disposed in the plurality of layers.

21. The material of claim 3 wherein an exterior surface of the solid rod is abraded to increase adhesion to the layers.

22. The method of claim 16 wherein the winding of additional fibers is repeated until the desired thickness of fiber layers is obtained.

23. The method of claim 16 wherein the first, second and additional fibers comprise a single fiber, a bundle of fibers, fiber tape, or fiber fabric.

24. The method of claim 16 wherein the metal shaft is hollow or solid.

25. The method of claim 16 wherein the metal shaft is cylindrical, triangular, rectangular, square or oval in cross-sectional shape.

26. The method of claim 16 wherein the metal shaft has a surface that is smooth, roughened, serrated, threaded or irregular.

27. The method of claim 16 wherein the first, second and additional fibers are wound in a consistent pattern along the entire length of the metal shaft.

28. The method of claim 16 wherein the fiber layers are not cured until all layers have been applied.

29. The method of claim 16 wherein each fiber layer is cured directly after application thereof.

30. The method of claim 18 wherein the filling is after the curing.

31. The method of claim 16 wherein the first, second, third and additional resin matrix material are not cured until all the impregnated fibers have been applied.

32. The method of claim 16 wherein each resin matrix material is cured directly after winding of the fiber thereon except for a last resin matrix material which is cured after application thereof.

* * * * *

UNITED STATES PATENT AND TRADEMARK OFFICE
CERTIFICATE OF CORRECTION

PATENT NO. : 8,298,664 B2  
APPLICATION NO. : 11/734292  
DATED : October 30, 2012  
INVENTOR(S) : Weitao Jia Page 1 of 1

It is certified that error appears in the above-identified patent and that said Letters Patent is hereby corrected as shown below:

In Col. 1, line 60, "teach using" should read --teaches using--.

In Col. 2, line 5, "teach a" should read --teaches a--.

In Col. 7, line 49, "herein are uniform" should read --herein is uniform--.

In Col. 8, line 9, "Sculpture ('?)" should read --Sculpture®--.

In Col. 9, line 59, Claim 12, "bismuth based filters" should read --bismuth based fillers--.

Signed and Sealed this  
Twenty-second Day of January, 2013

David J. Kappos  
*Director of the United States Patent and Trademark Office*